United States Patent [19]

Vitner

[11] 4,451,330

[45] May 29, 1984

[54] PROCESS FOR THE RECOVERY OF ALKALI METAL SALTS FROM AQUEOUS SOLUTIONS THEREOF

[75] Inventor: Joseph Vitner, Califon, N.J.

[73] Assignee: Kalama Chemical, Inc., Seattle, Wash.

[21] Appl. No.: 417,823

[22] Filed: Sep. 13, 1982

[51] Int. Cl.³ ............................................. B01D 1/16
[52] U.S. Cl. ................................................... 159/48.2
[58] Field of Search ................ 159/48.1, 48.2, 4 R, 159/4 CC, DIG. 10; 562/580, 593; 568/708

[56] References Cited

U.S. PATENT DOCUMENTS

| 2,193,336 | 3/1940 | Lecher | 260/621 |
| 3,023,252 | 2/1962 | Senior | 260/621 |
| 3,554,265 | 4/1971 | Milian | 159/48 |

FOREIGN PATENT DOCUMENTS 881906   5/1971   Canada .

Primary Examiner—Hiram H. Bernstein
Attorney, Agent, or Firm—Graybeal & Cullom

[57] ABSTRACT

In an integrated process for the recovery of alkakli metal phenates and carboxylates from aqueous solutions thereof, the aqueous solution is spray dried and the drying gas stream is contacted with an aqueous alkali metal salt solution which dissolves the particles of the alkali metal salt that were entrained in the drying gas stream. The salt-free inert gas stream is then dried, heated, and returned to the spray dryer.

10 Claims, 1 Drawing Figure

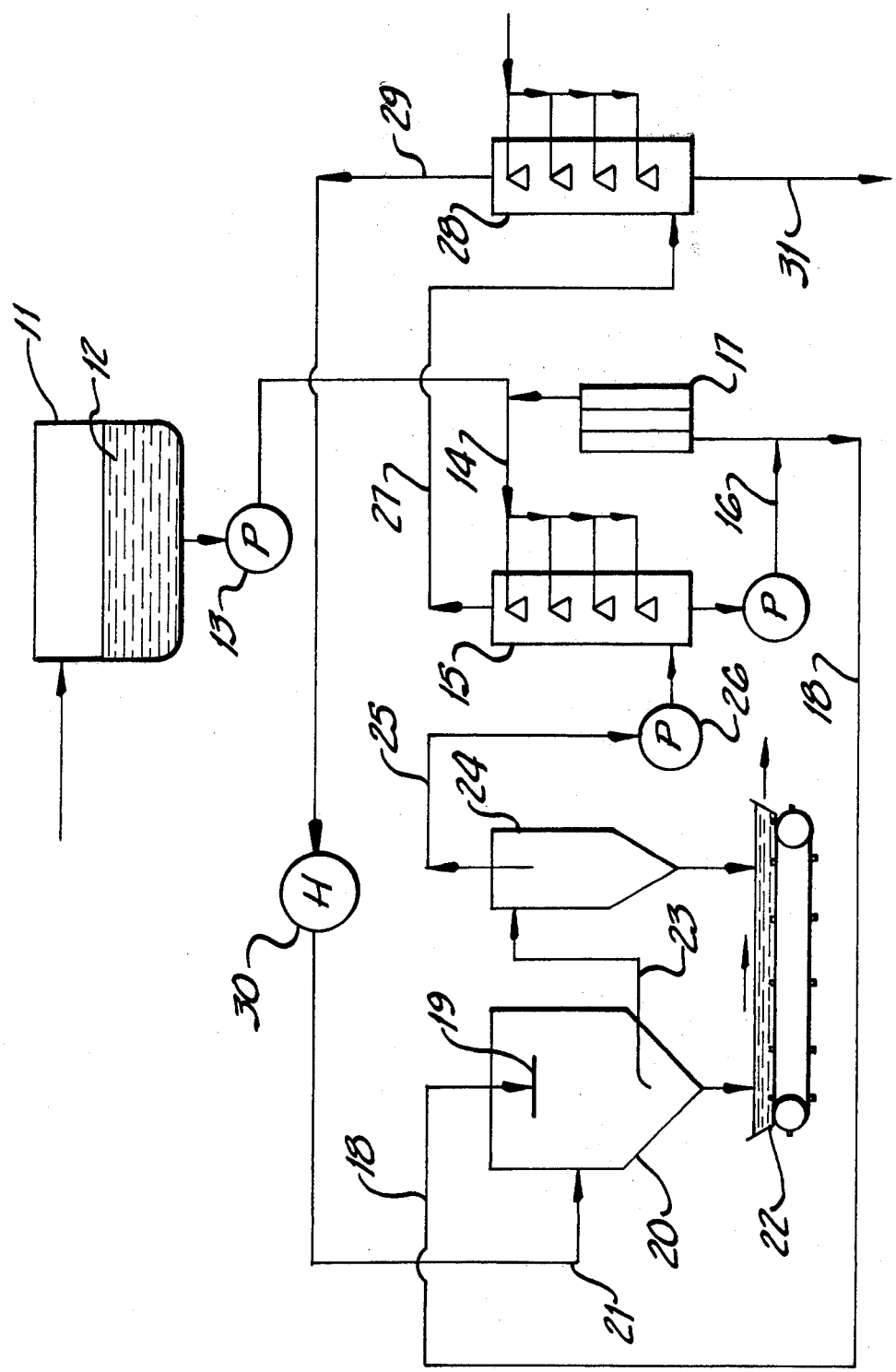

PROCESS FOR THE RECOVERY OF ALKALI METAL SALTS FROM AQUEOUS SOLUTIONS THEREOF

This invention relates to a process for the recovery of alkali metal salts from aqueous solutions thereof. More particularly, it relates to an integrated process for the production of substantially anhydrous, finely-divided alkali metal phenates and carboxylates.

Alkali metal phenates are used commercially in the production of hydroxyaromatic acids by the Kolbe process. In this process, the alkali metal phenates are reacted with carbon dioxide under pressure and in the absence of water to produce salicylic acid, p-hydroxybenzoic acid, and other hydroxyaromatic acids. The alkali metal phenate starting material is generally prepared by the reaction of a phenol with an alkali metal hydroxide in aqueous solution. Various methods have been proposed for the recovery of the alkali metal salts in substantially anhydrous form, but none has given entirely satisfactory results. For example, when an aqueous solution of an alkali metal phenate is dried in pans, the drying must be carried out at a relatively low temperature because rigorous heating causes decomposition and discoloration of the product. The resulting product, which contains small amounts of water, tends to cake and must be ground before it can be used industrially. A process for the spray drying of alkali metal phenate solutions under prescribed conditions was disclosed by Dege et al. in Canadian Pat. No. 881,906. This process results in the rapid drying of the alkali metal phenate and in the formation of a finely-divided product. In U.S. Pat. No. 3,554,265, Milian disclosed a procedure for the accurate and rapid determination of the amount of excess alkali metal hydroxide that is present in the aqueous alkali metal phenate solution that is used as the spray dryer feed solution.

In both the Dege et al. process and the Milian process, the gas stream leaving the spray dryer, which contains a considerable amount of alkali metal phenate particles, is passed into a cyclone separator where most of the entrained particles are recovered. The exit gas, which contains up to about 4 percent of the alkali metal phenate originally fed to the spray dryer, was vented to the atmosphere by Dege et al. Milian passed the exit gas containing entrained product particles through a water scrubber to dissolve the alkali metal phenate particles, and he discharged the resulting dilute alkali metal phenate solution to the sewer. In the practice of each of these processes, an appreciable amount of the product was lost, and air or water pollution problems were created.

In accordance with this invention, it has been found that finely-divided alkali metal salts can be recovered quantitatively from aqueous solutions thereof by means of an integrated process in which the aqueous salt solution is spray dried and the particles of the product that are entrained in the gas stream leaving the spray dryer are recovered. The exit gas from which the alkali metal salt particles have been removed is dried and recycled. Because all of the finely-divided product is recovered from the inert gas stream, quantitative yields of the dry finely-divided product are obtained, and there is no pollution of the atmosphere or of water.

In the process of this invention, an aqueous alkali metal salt solution is spray dried by the procedure disclosed in Canadian Pat. No. 881,906 and in U.S. Pat. No. 3,554,264, which are incorporated herein by reference. In this procedure an aqueous alkali metal salt solution is atomized, and the resulting spray is contacted with an inert gas stream that contains less than 0.5 percent by volume of carbon dioxide and that has been heated to a temperature in the range of 250° C. to 500° C. for the time required to effect dehydration and solidification of the alkali metal salt in the spray.

The hot inert gas stream leaving the spray dryer, which contains up to 20 percent, based on the weight of alkali metal salt in the aqueous solution that was charged to the spray dryer, of entrained particles of alkali metal salt, is passed into a cyclone separator where its content of entrained particles is reduced to about 4 percent, based on the weight of the alkali metal salt in the aqueous solution that was charged to the spray dryer. The inert gas stream leaving the cyclone separator is passed into a scrubber where it is brought into contact with an aqueous solution that contains 50 percent to 75 percent by weight of an alkali metal salt and that is maintained at a temperature in the range of 45° C. to 60° C., thereby dissolving the alkali metal salt particles in the alkali metal salt solution and cooling the inert gas stream to a temperature below 75° C., preferably to a temperature in the range of 45° C. to 70° C., and most preferably to a temperature in the range of 60° C. to 65° C. The aqueous alkali metal salt solution is then removed from the scrubber and divided into two portions. The first portion, which consists of 10 percent to 90 percent and preferably 10 percent to 50 percent of the solution, is cooled to a temperature in the range of 40° C. to 60° C. and preferably 50° C. to 55° C., and returned to the scrubber. The second portion, which consists of 10 percent to 90 percent and preferably 50 percent to 90 percent of the solution, is used as feed solution for the spray dryer.

The inert gas stream leaving the scrubber, which contains substantially no alkali metal salt, is passed into a second scrubber where it is contacted with water at a temperature in the range of 5° C. to 20° C. to cool and dry it. The resulting dried inert gas stream is then heated to a temperature in the range of 250° C. to 500° C., preferably 275° C. to 325° C., and returned to the spray dryer. The water leaving the second scrubber, which contains no alkali metal salt, is discharged to a waterway without creating pollution problems.

While the process of this invention is of particular value in the production of sodium phenate, which is used commercially in the manufacture of salicylic acid, it can also be used in the production of other alkali metal salts including alkali metal phenates and alkali metal carboxylates. The phenols whose alkali metal salt solutions can be used as the starting material in the process of this invention may be any mononuclear or polynuclear aromatic compound containing at least one hydroxyl group substituted in the aromatic nucleus. They may also have other nuclear substituents, such as alkyl groups, halogen atoms, amino groups, nitro groups, and the like. Illustrative of these phenols are the following: phenol, o-, m-, and p-cresols, p-aminophenol, m-nitrophenol, 2,4-dichlorophenol, pentachlorophenol, 1-naphthol, 2-naphthol, 5-amino-1-naphthol, 4-nitro-1 naphthol, 1-chloro-2-naphthol, and the like. The acids whose alkali metal salt solutions may be used in the practice of this invention include a wide variety of monocarboxylic and polycarboxylic aliphatic and aromatic acids, including hexanoic acid, decanoic acid, citric acid, ethylenediamine tetraacetic acid, hydroxymethylethylenediamine triacetic acid, benzoic acid, phthalic acid, tetrachlorophthalic acid, salicylic acid, sulfosalicylic acid, toluenesulfonic acid, and the like. Sodium and potassium are the most commonly used and the preferred alkali metal constituents of the salts. Salts of other metals of Group 1-A of the Periodic Table of the elements can also be used in the process of this invention.

The aqueous alkali metal salt solution that is used as the feed to the spray dryer comprises from about 50 percent to 75 percent by weight of one or more of the aforementioned alkali metal salts and from about 25 percent to 50 percent by weight of water. As is well known in the art, the aqueous alkali metal salt solutions may be prepared by reacting a phenolic compound or carboxylic acid in solid state, in molten state, or in solution or suspension in a suitable liquid with an alkali metal hydroxide, which may also be in the solid state, in solution, or in suspension. For example, the alkali metal salt solution may be prepared by dissolving a phenol or a carboxylic acid in a concentrated aqueous solution of an alkali metal hydroxide.

As is disclosed in Canadian Pat. No. 881,906, the spray drying of alkali metal salt solutions can be carried out in conventional spray drying equipment. Spray dryers usually consist of a means of atomizing the liquid feed, a source of hot gas, a drying chamber, and a means of separating the dry product from the exhaust gases. The spray dryer may be operated with concurrent or countercurrent gas flow. The use of countercurrent drying gas flow is preferred for the present purposes.

The inert drying gas that is used in this process must contain not more than about 0.5% by volume of carbon dioxide, since when greater amounts of carbon dioxide are present reactions which occur between the alkali metal salt and carbon dioxide yield undesirable by-products, such as unstable alkali metal phenylcarbonate, which will burn in the presence of oxygen. Consequently, both the yields and the quality of the product are adversely affected by the presence of more than about 0.5 percent by volume of carbon dioxide in the gas stream. Air, nitrogen, and other inert gases that contain less than about 0.5 percent by volume of carbon dioxide may be effectively employed as the drying gas in the spray drying process. The inert gas stream is usually at a temperature in the range of 250° C. to 500° C., preferably 275° C. to 325° C., when it enters the drying chamber of the spray dryer and at a temperature in the range of 110° C. to 150° C. when it leaves the drying chamber. It will be understood, however, that the exact temperature of the inert gas stream is not critical since the temperature need be only high enough to obtain the desired degree of dehydration and will depend in part upon the residence time of the gas stream in the drying chamber. Usually, the residence time will range from 5 to 30 seconds. In every case, the temperature of the inert gas stream must be maintained below the decomposition temperature of the alkali metal salt that is being dried. The spray drying step is ordinarily carried out under ambient pressure conditions.

The invention will be more completely understood when it is considered in conjunction with the accompanying drawing, which illustrates schematically the manner in which a preferred embodiment of this invention may be carried out.

As shown in the drawing, feed tank 11 contained an aqueous solution containing 65 percent by weight of sodium phenate. This solution 12, which was maintained at a temperature in the range of 90° C.–95° C. to prevent solidification in the unheated feed lines, was passed continuously through pump 13 and line 14 to scrubber 15. A portion of the sodium phenate solution leaving the scrubber through line 16 was passed through heat exchanger 17, where it was cooled to 50°–55° C., to line 14 which returned it to scrubber 15. The remainder of the sodium phenate solution was fed through line 18 to centrifugal atomizer 19 which atomized the solution in a horizontal plane. The droplets of feed solution fell continuously into chamber 20. Line 21 delivered air containing about 0.05 percent by volume of carbon dioxide, which had been heated to 300° C., into chamber 20, where the heated air countercurrently contacted the aqueous sodium phenate droplets and caused them to dry. The resulting finely-divided sodium phenate particles were fed to conveyor 22, which delivered them to the feed tank of a salicylic acid manufacturing plant. Outlet air which contained entrained sodium phenate particles and which was at a temperature of 120° C. was passed through line 23 into cyclone separator 24, where most of the entrained sodium phenate particles were separated from the gas stream and then fed to conveyor 22. The gas stream leaving the cyclone separator 24, which contained 3%–4% of the sodium phenate that was in the aqueous solution fed to the spray dryer, was passed through line 25 by means of blower 26 and into scrubber 15 where the finely-divided sodium phenate particles were dissolved in the circulating aqueous sodium phenate solution and the inert gas stream that left the scrubber through line 27 was cooled to 62° C. The cooled gas stream, which contained water vapor, was passed through the second scrubber 28 where it was further cooled by direct contact with cold water, thereby reducing its water content. The dried gas stream was then passed through line 29 to heater 30 which heated it to 300° C. The hot gas stream was returned through line 21 to spray dryer 20. The water leaving the second scrubber 28, which contained no sodium phenate, was discharged to the sewer through line 31.

The terms and expressions that have been employed are used as terms of description and not of limitation. There is no intention in the use of such terms and expressions of excluding any equivalents of the features shown and described or portions thereof. It is recognized that various modifications are possible within the scope of the invention claimed.

What is claimed is:

1. An integrated process for the production of substantially anhydrous, finely-divided particles of an alkali metal salt selected from the group consisting of alkali metal phenates and alkali metal carboxylates that comprises the following sequential steps:
   (a) atomizing an aqueous solution containing 50 percent to 75 percent by weight of said alkali metal salt;
   (b) contacting the resulting spray with a stream of inert gas that contains less than 0.5 percent by volume of carbon dioxide and that has been heated to a temperature in the range of 250° C. to 500° C. for the time required to effect dehydration and solidification of the alkali metal salt in said spray;
   (c) separating substantially anhydrous, finely-divided particles of the alkali metal salt from a hot outlet inert gas stream that contains up to 20 percent, based on the weight of alkali metal salt in the aqueous solution that was atomized in Step (a), of entrained particles of the alkali metal salt;

(d) passing said inert gas stream through a separator, thereby reducing its content of entrained alkali metal salt particles to 3 percent to 4 percent by weight, based on the weight of alkali metal salt in the aqueous solution that was atomized in Step (a);

(e) passing said inert gas stream into a scrubber that contains an aqueous solution that contains 50 percent to 75 percent by weight of said alkali metal salt and that is maintained at a temperature in the range of 45° C. to 60° C., thereby dissolving said entrained alkali metal salt particles in said alkali metal salt solution and cooling the inert gas stream to a temperature below 75° C.;

(f) cooling the inert gas stream from which entrained salt particles were removed in Step (e) by contacting it with water at a temperature in the range of 5° C. to 20° C., thereby obtaining a dried inert gas stream;

(g) heating the dried inert gas stream to a temperature in the range of 250° C. to 500° C.;

(h) contacting the hot inert gas stream from Step (g) with the atomized aqueous alkali metal salt solution formed in Step (a);

(i) repeating Steps (c) through (h);

(j) removing from the scrubber the aqueous alkali metal salt solution in which particles of alkali metal salt were dissolved in Step (e);

(k) dividing said solution into a first portion that consists of 10 percent to 90 percent of the solution and a second portion that consists of 10 percent to 90 percent of the solution;

(l) cooling said first portion to a temperature in the range of 40° C. to 60° C. and returning it to the scrubber;

(m) feeding said second portion to the atomizer; and (n) repeating Steps (a) through (c) and Steps (j) through (m).

2. The process of claim 1 wherein the alkali metal salt is sodium phenate.

3. The process of claim 1 wherein the solution that is atomized in Step (a) contains 65 percent by weight of sodium phenate.

4. The process of claim 1 wherein in Step (b) the gas stream has been heated to a temperature in the range of 275° C. to 325° C.

5. The process of claim 1 wherein the solution in which the alkali metal salt particles are dissolved in Step (e) contains 65 percent by weight of the alkali metal salt.

6. The process of claim 1 wherein in Step (e) the inert gas stream is cooled to a temperature in the range of 45° C. to 70° C.

7. The process of claim 1 wherein in Step (e) the inert gas stream is cooled to a temperature in the range of 60° C. to 65° C.

8. The process of claim 1 wherein in Step (g) the dried inert gas stream is heated to a temperature in the range of 275° C. to 325° C.

9. The process of claim 1 wherein in Step (k) the solution is divided into a first portion that consists of 10 percent to 50 percent of the solution and a second portion that consists of 50 percent to 90 percent of the solution.

10. The process of claim 1 wherein in Step (l) said first portion of the solution is cooled to a temperature in the range of 50° C. to 55° C.

* * * * *